US009044289B2

(12) United States Patent
Wiener (10) Patent No.: US 9,044,289 B2
(45) Date of Patent: Jun. 2, 2015

(54) UNIVERSAL TRANSITIONAL ABUTMENT (76) Inventor: Joseph Wiener, Vandalia, OH (US)

(*) Notice: Subject to any disclaimer, the term of this patent is extended or adjusted under 35 U.S.C. 154(b) by 166 days.

(21) Appl. No.: 12/364,031

(22) Filed: Feb. 2, 2009

(65) Prior Publication Data
US 2009/0197218 A1 Aug. 6, 2009

Related U.S. Application Data (60) Provisional application No. 61/026,168, filed on Feb. 5, 2008, provisional application No. 61/036,601, filed on Mar. 14, 2008.

(51) Int. Cl.
A61C 8/00 (2006.01)

(52) U.S. Cl.
CPC ............... A61C 8/005 (2013.01); A61C 8/0053 (2013.01)

(58) Field of Classification Search
CPC .......... A61C 1/084; A61C 8/00; A61C 8/001;
A61C 8/0006; A61C 8/0012; A61C 8/0013;
A61C 8/0018; A61C 8/0019; A61C 8/0022;
A61C 8/0033; A61C 8/0036; A61C 8/0039;
A61C 8/0048; A61C 8/005; A61C 8/0053;
A61C 8/0054; A61C 8/0057; A61C 8/0059;
A61C 8/006; A61C 8/0065; A61C 8/0066;
A61C 8/0068; A61C 8/0069; A61C 8/0075;
A61C 8/0077; A61C 8/0078; A61C 8/008;
A61C 8/0086; A61C 8/0089; A61C 13/0004;
A61C 13/2656
USPC ................ 433/172–176, 26, 191, 196, 201.1,
433/202.1, 215, 220–221
See application file for complete search history.

(56) References Cited

U.S. PATENT DOCUMENTS 1,507,231 A 9/1924 Cressler
1,802,405 A * 4/1931 Cressler ........................ 433/204
4,187,609 A * 2/1980 Edelman ....................... 433/176
(Continued)

FOREIGN PATENT DOCUMENTS

DE 20 2007 005 474 U1 8/2007

OTHER PUBLICATIONS

Machine translation of DE 20 2007 005 474 (cited on Jun. 5, 2014 IDS), Straumann Holding AG, Aug. 2, 2007.*
(Continued)

Primary Examiner — Cris L Rodriguez
Assistant Examiner — Justin O'Donnell
(74) Attorney, Agent, or Firm — Dinsmore & Shohl LLP (57) ABSTRACT A universal transitional abutment for immediate placement during the first and/or second stages of the dental implant surgery is presented. The transitional dental abutment can approximate the natural appearance of a patient's own tooth. The transitional dental abutment can bypass the traditional anti-rotational component common to most dental implant systems by directly screwing the transitional dental abutment onto a dental implant. In another embodiment, the abutment can be a universal anterior transitional abutment. The anterior transitional dental abutment can include a ball and a crown. The ball can be affixed to the dental implant and the crown snaps onto the ball. The transitional dental abutment can be universally used on most dental implants regardless of manufacturer by simply changing the fastener of the transitional dental abutment. The universal transitional abutments can be permanent. Additionally, the universal transitional abutments can be readily available and cost effective to the dental professional.

17 Claims, 4 Drawing Sheets

(56) References Cited

U.S. PATENT DOCUMENTS

| | | | |
|---|---|---|---|
| 4,793,808 A * | 12/1988 | Kirsch | 433/173 |
| 5,015,186 A * | 5/1991 | Detsch | 433/173 |
| 5,071,345 A | 12/1991 | Rosen | |
| 5,169,309 A | 12/1992 | Staubli et al. | |
| 5,259,759 A | 11/1993 | Jorneus et al. | |
| 5,316,477 A | 5/1994 | Calderon | |
| 5,336,090 A | 8/1994 | Wilson, Jr. et al. | |
| 5,338,196 A | 8/1994 | Beaty et al. | |
| 5,417,570 A | 5/1995 | Zuest et al. | |
| 5,439,380 A | 8/1995 | Marlin | |
| 5,564,922 A | 10/1996 | Rosa et al. | |
| 5,599,185 A * | 2/1997 | Greenberg | 433/173 |
| 5,651,675 A | 7/1997 | Singer | |
| 5,662,475 A * | 9/1997 | Mena | 433/172 |
| 5,674,069 A | 10/1997 | Osorio | |
| 5,674,071 A | 10/1997 | Beaty et al. | |
| 5,759,036 A | 6/1998 | Hinds | |
| 5,829,977 A | 11/1998 | Rogers et al. | |
| 5,876,204 A | 3/1999 | Day et al. | |
| 5,915,967 A | 6/1999 | Clokie | |
| 5,931,675 A | 8/1999 | Callan | |
| 5,989,028 A * | 11/1999 | Niznick | 433/173 |
| 6,048,203 A | 4/2000 | Rosenberg | |
| 6,050,819 A | 4/2000 | Robinson | |
| 6,067,701 A | 5/2000 | Vandewalle | |
| 6,126,662 A | 10/2000 | Carmichael et al. | |
| 6,129,548 A | 10/2000 | Lazzara et al. | |
| 6,152,737 A | 11/2000 | Beaty et al. | |
| 6,168,436 B1 | 1/2001 | O'Brien | |
| 6,227,856 B1 | 5/2001 | Beaty et al. | |
| 6,250,922 B1 | 6/2001 | Bassett et al. | |
| 6,283,753 B1 | 9/2001 | Willoughby | |
| 6,325,628 B1 | 12/2001 | Morgan | |
| 6,368,108 B1 | 4/2002 | Locante et al. | |
| 6,464,500 B1 | 10/2002 | Popovic | |
| 6,497,573 B2 | 12/2002 | Wagner et al. | |
| 6,500,003 B2 * | 12/2002 | Nichinonni | 433/173 |
| 6,663,387 B2 * | 12/2003 | Riley | 433/173 |
| 6,663,388 B1 | 12/2003 | Schar et al. | |
| 6,716,030 B1 | 4/2004 | Bulard et al. | |
| 6,733,292 B2 * | 5/2004 | Odrich et al. | 433/173 |
| 6,746,244 B2 | 6/2004 | Riley et al. | |
| 6,793,491 B2 | 9/2004 | Klein et al. | |
| 7,287,982 B2 | 10/2007 | Riley et al. | |
| 2003/0198920 A1 | 10/2003 | Lin | |
| 2004/0152047 A1 | 8/2004 | Odrich et al. | |
| 2004/0166477 A1 * | 8/2004 | Lans | 433/215 |
| 2004/0241614 A1 | 12/2004 | Goldberg et al. | |
| 2005/0048440 A1 * | 3/2005 | Feng | 433/175 |
| 2006/0046229 A1 * | 3/2006 | Teich | 433/173 |
| 2009/0123891 A1 | 5/2009 | Rosenberg | |
| 2011/0008755 A1 | 1/2011 | Misch | |

OTHER PUBLICATIONS

Johnstone, Dental Implants, http://www.yourdentistryguide.com/implants/, Jan. 30, 2008.
Wohrle, Single-Tooth Replacement in the Aesthetic Zone with Immediate Provisionalization: Fourteen Consecutive Case Reports, Practical Periodontics & Aesthetic Dentistry 1998;10(9):1107-1114.
Official Notification directed to Israeli patent application No. 207373 dated Jul. 1, 2012.
International Search Report, Application No. PCT/US2012/041980, Filed Jun. 12, 2012.
Written Opinion, Application No. PCT/US2012/041980, Filed Jun. 12, 2012.
International Search Report and Written Opinion dated Jul. 28, 2009 pertaining to International Application No. PCT/US2009/032914.
International Search Report pertaining to International Application No. PCT/US2012/041980, filed Jun. 12, 2012.
Written Opinion pertaining to International Application No. PCT/US2012/041980, filed Jun. 12, 2012.
Johnstone, Dental Implants, http://www.yourdentistryguide.com/Implants/, Jan. 30, 2008, pp. 1-3.
Wohrle, Single-Tooth Replacement in the Aesthetic Zone with Immediate Provisionalization: Fourteen Consecutive Case Reports, Practical Periodontics & Aesthetic Denistry 1998; 10(9) pp. 1107-1114.
Bozkaya et al., Mechanics of the Tapered Interference Fit in Dental Implants, Journal of Biomechanics, 2003 Elsevier Science Ltd., doi: 10.1016/S0021-9290(03)001775, pp. 1649-1658.
Standard Tapers—http://books.google.com/books?id=88nePuMEdxAC&pg-PA245&dq-morse+taper+angle&hl=en&sa=X&ei=3tDAUa74JaaSiQLRx4DIBg&ved=0CDkQ6AEwAA#v=onepage&q=morse%20taper%20angle&f-false, pp. 245-248.
Little Machine Shop, Morse Tapers—http://littlemachineshop.com/Reference/Tapers.php.

* cited by examiner

UNIVERSAL TRANSITIONAL ABUTMENT

CROSS-REFERENCE TO RELATED APPLICATIONS

This application claims the benefit of U.S. Provisional Application Ser. Nos. 61/026,168, filed Feb. 5, 2008, and 61/036,601, filed Mar. 14, 2008.

BACKGROUND

The present disclosure generally relates to transitional abutments for use in dental implant surgical procedures and, in particular, relates to a universal transitional abutments for use in dental implant surgical procedures that can be used regardless of the dental implant manufacturer.

A dental implant is an artificial tooth root replacement. A typical implant consists of a titanium screw (resembling a tooth root) with a roughened surface. An osteotomy, or precision hole, is carefully drilled into jawbone and the implant is installed in the osteotomy. The most common treatment plan calls for several surgeries over a period of months. Quite a few manufacturers make dental implants including Bicon Dental Implants, BioHorizons, Nobel Biocare, Straumann, Osteocare, Osteo-Ti, 3i, Zimmer, Astra Tech, Ankylos, Implant Direct, Intra-Lock, Lifecore, Bio-Lok and Diskimplant to name a few.

Healing and integration of the implant with jawbone occurs over several months in a process called osseointegration. At the appropriate time, the dental professional uses the implant to anchor a permanent crown. The dental professional can be, for example, a oral surgeon, a periodonist, general dentist, or any suitable dental professional. Since the implants supporting the restoration are integrated, which means they are biomechanically stable and strong, the patient is immediately able to masticate (chew) normally.

During the first stage, or immediate loading, of the dental implant procedure, at edentulous (without teeth) jaw sites, a pilot hole is bored into the recipient bone, taking care to avoid vital structures. Once properly torqued into the bone, a cover screw is placed on the implant, then the gingiva or gum is sutured over the site and allowed to heal for several months for osseointegration to occur between the titanium surface of the implant and jawbone. This stage results in an unattractive gap in teeth of the patient where the permanent crown of the implant will eventually go. The dental professional, or a dental laboratory, could fabricate a custom first stage temporary abutment to fit over the cover screw and to fill the gap. However, in general, such a temporary abutment is expensive in terms of both time and cost. Therefore, this procedure is rarely done at this stage even though it is frequently requested by the patient.

After what could be several months, a second stage of the dental implant procedure is performed. The implant is uncovered in another surgical procedure, usually under local anesthetic by the dental professional, and a healing abutment is placed onto the implant. The healing abutment can protrude through the gum tissue of the mouth. This healing abutment encourages the gum to grow in the right scalloped shape to approximate a natural tooth's gums and allows assessment of the final aesthetics of the restored tooth. The healing abutments are typically made from a titanium alloy and therefore are silver in color. Consequently, the patient will then have a silver post protruding through the gum at the site of the dental implant. Therefore, the titanium post can be physically unappealing and can be visible to the eye from weeks to months. Once the correct gum growth has occurred, a third, and final, stage of the dental implant procedure is performed and a permanent crown will be fabricated and placed on the implant and locked into place.

When dental implants are placed in the anterior portion of the mouth, the thickness of the bone at that point will determine the angulation of the dental implant. If the patient has suffered trauma in that area, or is edentulous, or for any other reason such as periodontitis, the bone in the anterior maxilla, or upper jaw, or the bone in the anterior mandible, or lower jaw, may be compromised. Having the bone be comprised can occur quite frequently. When bone compromise occurs, the dental professional will have to angulate, or tilt, the dental implant either in the labial direction (i.e., towards the face) or in the lingual direction (i.e., towards the tongue). Only in a small percentage of time is the dental professional able to place the anterior dental implant directly in line with the long axis of the restoration.

In order to correct for any angle discrepancies, the dental professional typically would have to purchase an angulated titanium abutment or custom create a gold or ceramic abutment. A custom created temporary crown could cost the dental professional between about $150 to about $700 and would require weeks to create. Additionally, the typical custom temporary crown would require an indirect impression technique to be performed requiring at least two office visits for the patient.

In general, the traditional denture restoration systems use a cap or an "O" ring that employ a ball and socket type fixation. In these systems, a ball abutment is typically permanently screwed into the dental implant. A keeper, or socket, is formed into the denture into which an "O" ring is locked. This "O" ring interacts with the ball abutment to maintain the denture on the ball abutment. Typically, the denture and the "O" ring are removable for hygiene and maintenance and are not permanently installed in the patient's mouth. Additionally, the typical ball and socket systems are not used to correct or any angle discrepancies. Examples of ball and socket systems are Dalla Bona—ORS ("O" Ring System), Allegro OTCap, Gijin Compact, Uni-anchor and Flexi Post.

Therefore, there is a need for a transitional dental abutment that approximates the natural appearance of a patient's own tooth in terms of anatomical structure and color.

There is also a need for a transitional dental abutment that can be universally used by a dental professional regardless of the manufacturer of the implant, readily available, and cost effective.

There is an additional need for an anterior universal transitional abutment that is permanent, inexpensive and easily installed.

BRIEF SUMMARY

According to the present disclosure, an universal transitional dental abutment for immediate placement during the first and/or second stages of the dental implant surgical procedure is presented. The transitional dental abutment will approximate the natural appearance of the patient's own tooth. The transitional dental abutment can bypass the traditional anti-rotational component common to most dental implant systems by merely directly screwing the transitional dental abutment on the dental implant. An anterior transitional dental abutment will comprise a ball component and a crown component. The ball component can comprises a collar section that abuts the dental implant. The collar section can have substantially the same diameter of the dental implant. The ball component can be affixed to the dental implant by a screw and the crown component snaps onto the ball component. The transitional dental abutment can be universally used on most dental implants regardless of manufacturer by simply changing the fastener of the anterior transitional dental abutment.

Accordingly, it is a feature of the embodiments to provide for a universal transitional dental abutment during the first and second stages of dental implant surgical procedure that approximate the natural appearance of the patient's own tooth in terms of anatomical structure and tooth color.

It is another feature of the embodiments to provide for an anterior universal transitional dental abutment during the first and second stages of dental implant surgical procedure that approximate the natural appearance of the patient's own tooth in terms of anatomical structure and tooth color.

It is yet another feature of the embodiments, to provide a universal transitional dental abutment that can be universally used regardless of the manufacturer of the dental implant, permanent, readily available and cost effective. Other features of the embodiments will be apparent in light of the description herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Figure 1:
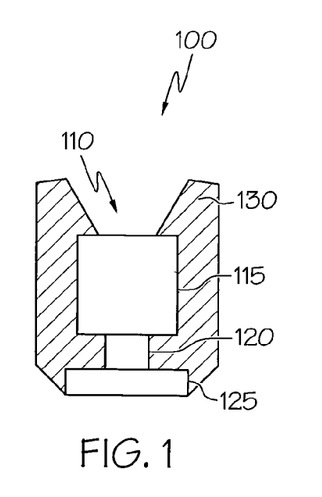
FIG. 1 illustrates a generic dental abutment according to an embodiment.

Referring to FIG. 1, a generic universal transitional dental abutment 100 is illustrated. The dental abutment 100 can comprise a crown body 130 and an opening 110. The opening 110 can extend through the entire length of crown body 130 of the dental abutment 100. The opening 110 can be located approximately in the center of the dental abutment 100. The opening 110 can be comprised of three sections: a top section 115, a middle section 120, and a bottom section 125. Each section can have a different diameter. For example, the middle section 120 can be narrower than the top section 115 and the bottom section 125. The top section 115 can have a diameter of about 5 mm to about 12 mm, the middle section can have a diameter of approximately 5 mm to approximately 12 mm, and the bottom section 125 can have a diameter of about 4 mm to about 5 mm. The dental abutment 100 can be designed to fit the opening 110 over a typical titanium dental implant during the second stage of a typical dental implant surgical procedure. The opening 110 thereby can allow access to the dental implant.

Figure 2A:
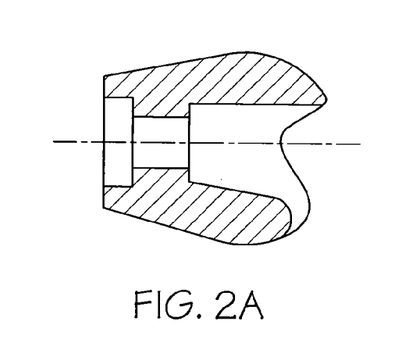
FIG. 2A illustrates a section view of a bicuspid dental abutment according to an embodiment.
Figure 2B:
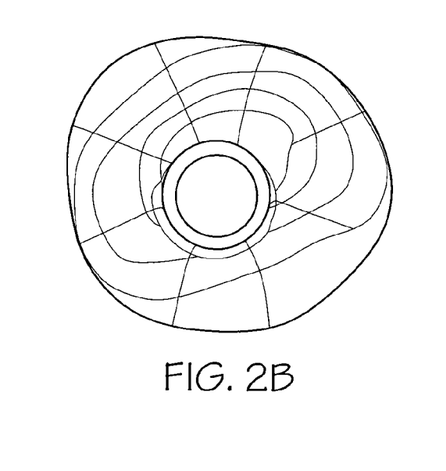
FIG. 2B illustrates a top view of a bicuspid dental abutment according to an embodiment.
Figure 2C:
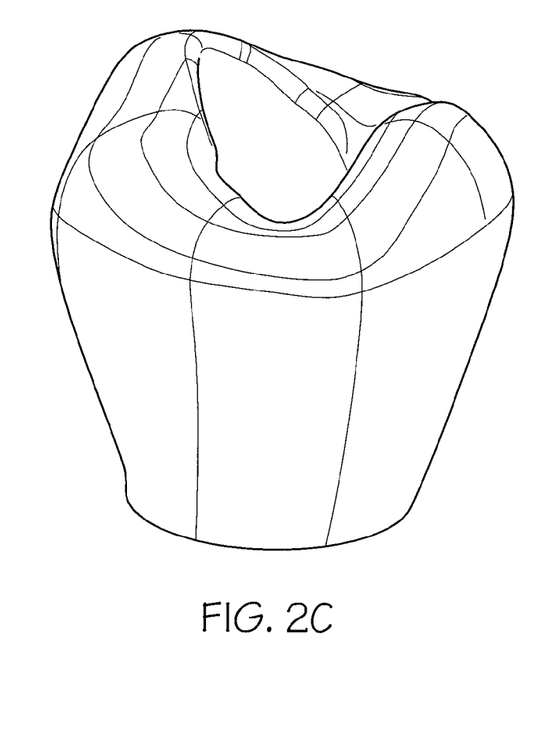
FIG. 2C illustrates a perspective view of a bicuspid dental abutment according to an embodiment.
Figure 3A:
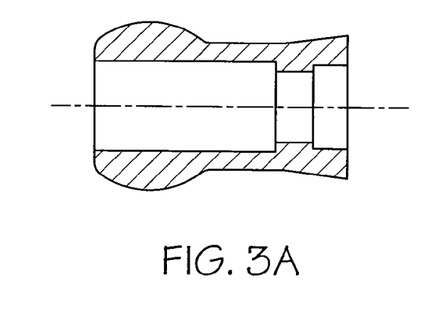
FIG. 3A illustrates a section view of a molar dental abutment according to an embodiment.
Figure 3B:
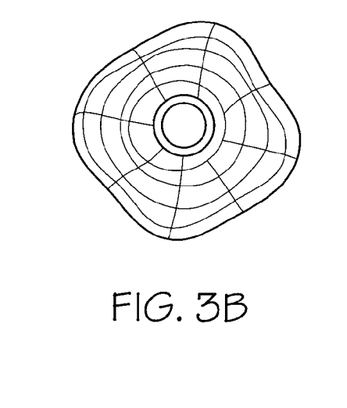
FIG. 3B illustrates a top view of a molar dental abutment according to an embodiment.

The crown body 130 of the universal transitional dental abutment 100 can be comprised of acrylic or any other suitable material known in the art for use as in traditional temporary dental abutment. The material for forming the crown body 130 of the universal transitional dental abutment 100 can be blown into a mold in a method as is typically known in the art. The crown body 130 can be shaped to resemble the typical natural anatomical shape of the tooth. For example, in one embodiment, the universal transitional dental abutment 100 can be shaped to approximate the shape of a bicuspid, as illustrated in FIGS. 2A-C. Alternatively, in another embodiment, the universal transitional dental abutment 100 can be shaped to approximate the shape of a molar tooth, as illustrated in FIGS. 3A-B. A molar dental abutment 100 can have a length that ranges from about 9 mm to about 12 mm, a width of about 8 mm to about 12 mm, and a diameter of approximately 4 mm to approximately 6 mm. A pre-molar dental abutment 100 can have a length that ranges from about 5 mm to about 8 mm, a width of about 5 mm to about 7 mm, and a diameter of approximately 2.5 mm to approximately 3.5 mm. In addition, the color of the universal transitional dental abutment 100 can be shaded to approximate the natural coloring of the patient's own teeth.

In the initial stage of the surgery, as discussed above, a dental implant body can be integrated into the jaw bone of the patient as is known in the art. The dental abutment 100 can be then placed over the dental implant protruding through the gum of the patient. A screw can be positioned through the opening 110 of the dental abutment 100 and can be threaded into the dental implant. The screw can be any suitable dental screw known in the art. A torque screwdriver can be used to drive the screw through the dental abutment 100 and into the dental implant. The torque screwdriver can be set to the dental implant's manufacturer's specifications to prevent the dental abutment 100 from becoming loose. The universal transitional dental abutment 100 can have a smaller mesial and distal width and a shorter occlusial height than the traditional healing abutment typically used. The universal transitional dental abutment 100 can be used with almost all dental implants by simply directly screwing the universal transitional dental abutment 100 onto the dental implant.

Anti-rotational devices are traditionally used to prevent the dental abutment from coming loose during function, such as, for example, chewing. The anti-rotational component are typically used by the dental professional when affixing the permanent crown to the final abutment during the third stage of the dental implant procedure. The anti-rotational device used in traditional dental implants can be one of several types, such as, for example, internal hexagonal, external hexagonal, internal octagonal, or Moore taper, to name a few. However, directly screwing the dental abutment 100 to the dental implant, in a effect, can allow the universal transitional dental abutments 100 to bypass the anti-rotational component typically found in almost all dental implant systems. By bypassing the anti-rotational device, the universal transitional dental abutment 100 can sit directly on the shoulder of the dental implant while being affixed to the dental implant with the screw. Because the universal transitional dental abutment 100 can be placed on the dental implant temporarily, coming loose cannot be an issue. Additionally, because the universal transitional dental abutment 100 can fit over and affixed to most dental implants with a simple screw, the dental transitional dental abutment 100 can be used universally.

The dental professional can select the size of universal transitional dental abutment 100 to used based on the size of the dental implant system being used, regardless of the manufacturer of the dental implant system. For example, a 4 mm universal transitional dental abutment can be used for all 4 mm dental implant systems, a 5 mm universal transitional dental abutment for all 5 mm dental implant systems, and so on. In other words, the diameter of the bottom section 125 of the opening 110 can be coordinated to fit over the diameter of the dental implant being used by the dental professional.

The dental professional can adapt the universal transitional dental abutment 100 to different dental implant systems from different manufacturers by simply changing the fastener method, i.e., changing the type of screw used, of the universal transitional dental abutment 100. Different dental implants can have, for example, different screw threads, diameters, and screw head sizes. Therefore, different screw types can be manufactured to affix the universal transitional dental abutment 100 to the different types of dental implants. By using universal transitional dental abutment 100, in this embodiment, the patient can have aesthetically pleasing restoration abutment from second stage of the dental implant surgical procedure until the permanent crown is installed.

Figure 4:
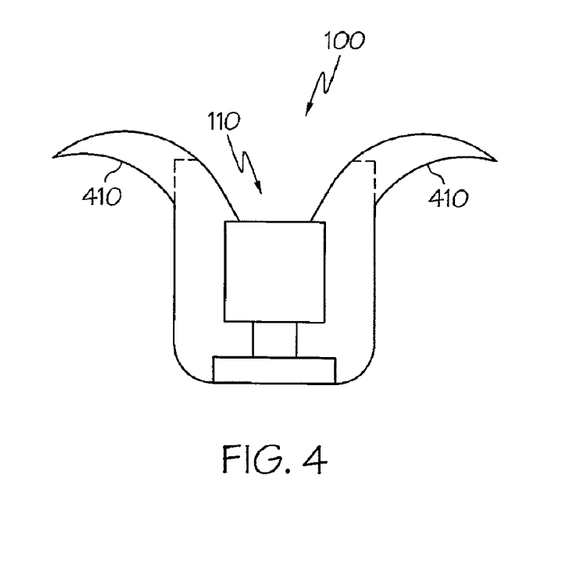
FIG. 4 illustrates a generic dental abutment according to an embodiment.

In another embodiment, the universal transitional dental abutment 100 can be designed to fit with a provisional abutment during the first stage, or immediate loading, of the dental implant surgical procedure by simply adapting the universal transitional dental abutment 100 described above to fit with the dental implant at the first stage. In this embodiment, a pre-surgical model can be fabricated. The dental professional can use universal transitional dental abutment 100 as a surgical guide by placing the universal transitional dental abutment 100 in the patient's mouth. The universal transitional dental abutment 100 can be affixed in the mouth by winged composite retainers 410 that can be made from the pre-surgical model as illustrated in FIG. 4. The dental professional then can place a pilot drill down the center of the universal transitional dental abutment 100 through its opening 110 to create the pilot hole in the jawbone for the dental implant. The dental implant can then be placed in the jaw. The winged composite retainers 410 can then be removed and the universal transitional dental abutment 100 can be screwed into place as was discussed above. Therefore, using this embodiment, the patient can have an aesthetically pleasing restoration abutment from first stage of the dental implant surgical procedure all the way until the permanent crown is installed in the third stage. In other words, in this embodiment, by installing the universal transitional dental abutment in the first stage, the patient may skip the second stage of the dental implant surgery.

Figure 5:
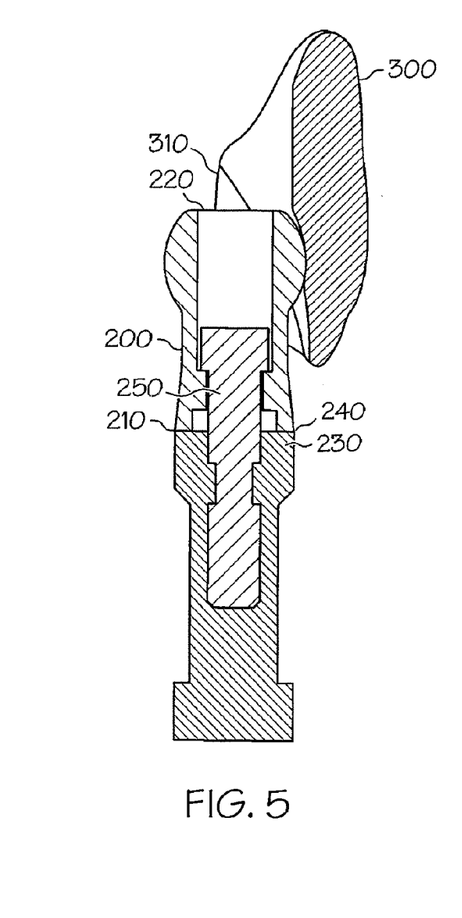
FIG. 5 illustrates a planar view of the anterior dental abutment according to an embodiment.

In yet another embodiment, the universal transitional abutment can be affixed to the dental implant located in the anterior portion of the mouth. In this embodiment, the anterior universal transitional abutment can comprise of two components: a ball 200 and crown 300. Referring to FIG. 5, the ball component 200 of an anterior universal transitional abutment is illustrated. The ball component 200 can be occlusal. The ball component 200 can be comprised of acrylic, titanium, or any other suitable material. The ball component 200 can have a length of approximately 5 mm to approximately 10 mm, a width of about 2.8 mm to about 3.5 mm, and a diameter of approximately 3.5 mm to approximately 4 mm. The ball component 200 can fit over a typical dental implant 230 and can comprise a flat portion 210, or collar, that can abut and make intimate contact with the shoulder area 240 of the dental implant 230. The ball component 200 can have a variety of collar 210 depths ranging from about 1 mm to about 5 mm to match with a variety of different dental implant 230 systems. The ball component 200 can be affixed to the dental implant 230 with a screw 250 through the center 220 of the ball component 200 as is known in the art. Retention grooves can be located over the external surface of the ball component 200. The retention grooves can help secure the crown component 300 to the ball component 200.

The crown component 300 of the anterior universal transitional abutment can have a length of approximately 6 mm to approximately 12 mm, a width of about 4 mm to about 10 mm, and a diameter of approximately 2.5 mm to approximately 6 mm. The crown component 300 can be made of acrylic or any similar type material known in the art. The crown component 300 can snap onto the ball component 200 of the anterior universal transitional abutment and can be rotated approximately 360° clockwise or counter-clockwise on the ball component 200 as needed. Additionally, the crown component 300 can be rotated in the labial (forward) direction or the lingual (backwards) direction on the ball component 200 as needed. In one exemplary example, the crown component 300 can be rotated approximately 24° in the buccal labial direction. In addition, the crown component 300 can have an open slot 310. The crown component 300 approximates the natural appearance of an anterior tooth.

The anatomical shapes of the crown components 300 that can be available are the left or right upper cuspids (tooth numbers 6 and 11), left or right upper lateral incisor (tooth numbers 7 and 10), left or right upper central incisor (tooth numbers 8 and 9), lower left or right cuspids (tooth numbers 27 and 22), left or right lower lateral incisor (tooth numbers 26 and 23), or left or right lower central incisor (tooth numbers 25 and 24).

For those dental implant systems that cannot accept the universal transitional abutment, a one-piece abutment can be made out of polycarbonate material or metal titanium using the same size ball component 200. The crown components 300 can still be used to snap onto the one or two piece abutment.

Figure 6:
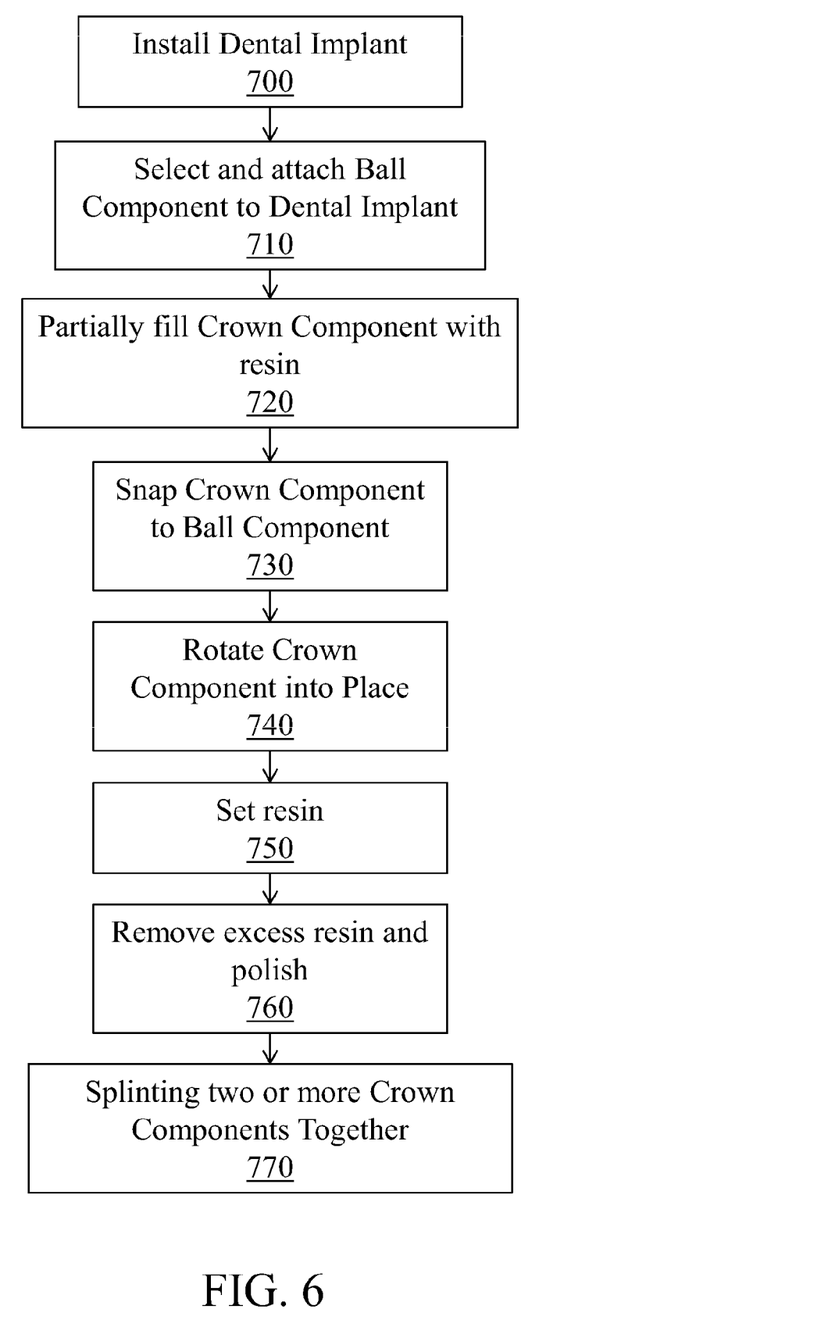
FIG. 6 is a flow chart illustrating a method installing an anterior dental abutment according to an embodiment.

FIG. 6 is a flow chart illustrating a method installing an anterior dental abutment. In step 700, a dental implant 230 is surgically installed into the jaw of a patient. Using an anterior universal transitional abutment, the dental professional, during either the first or second stage of the surgery, can select a ball component 200 with the proper collar 210 depth (i.e., 1-5 mm) needed to attach to the dental implant 230 and can screw that ball component 200 of the anterior universal transitional abutment onto the dental implant 230 in step 710. The dental professional can then fill the screw access hole with a dental filling material that is known in the art. The dental professional can select the proper crown component 300 for the anterior universal transitional abutment and can partially fill the crown component 300 with any number of available resin material known in the art in step 720. After partially filling the crown component 300, the dental professional can snap the crown component 300 on the ball component 200 in step 730. Any excess resin material can exit the slot 310 located on the crown component 300. The crown component 300 can then be rotated into the proper position in step 740 and the resin material can be set in step 750 by light activation, by self activation or by any other method known in the art. The dental professional can remove any excess material and can polish the crown component 300 in step 760. Using this method, the crown component 300 can be affixed rigidly and permanently to the ball component 200. This procedure can be accomplished in a very short period, on the average of ten minutes, in the dental professional's office and at a low cost to the dental professional.

In another embodiment, the dental professional can either remove or leave the ball component 200 of the anterior universal transitional dental abutment and can use a temporary cement known in the art to affix the crown component 300 to the universal transitional dental abutment. This embodiment can enable the dental professional's retrievability when making the final restoration.

If splinting 770 (i.e., affixing two or more crowns components together) is desired, two or more dental implants can be placed in the bone. The dental professional can form retention grooves mesially, or on the left side, or distally, on the right side, of the crown component 300 to better affix the crowns together. The dental professional can place resin material into the retention grooves. The resin material can be set by light activation, by self activation or by any other method known in the art. After setting, the dental professional can polish the crown component 300.

Because one size of the universal transitional dental abutment can fit on all dental implant systems of that particular size, the universal transitional dental abutments can be readily available to the dental professional for the patients who request them. Additionally, the one size fits all aspect of the universal transitional dental abutment can also help the dental professional maintain smaller inventories of dental implant system components to those that he or she uses, thereby, reducing costs.

It is noted that terms like "preferably," "commonly," and "typically" are not utilized herein to limit the scope of the claims or to imply that certain features are critical, essential, or even important to the structure or function of the claims. Rather, these terms are merely intended to highlight alternative or additional features that may or may not be utilized in a particular embodiment of the present disclosure.

For the purposes of describing and defining the present disclosure it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

What is claimed is:

1. A transitional anterior dental implant abutment for attachment to a pre-existing dental implant by a screw in a patient during a first stage or a second stage of a dental implant surgery, the transitional anterior dental implant abutment consisting of:
    an occlusal ball component, wherein the ball component is configured to fit over and attach to the pre-existing dental implant and to bypass an anti-rotational feature of the pre-existing dental implant; and
    a crown component consisting of a single, unitary structure having a frontward facing portion and a rearward facing portion, wherein the frontward facing portion defines a continuous outer surface which approximates the natural appearance of an anterior tooth and is configured to protrude through gum tissue of the patient, and wherein the rearward facing portion has an open slot, wherein the crown component snaps onto the ball component and directly contacts the ball component, and wherein the crown component is rotatable 360° clockwise or counter-clockwise after snapping on to the ball component, such that:
        upon the attachment of the transitional anterior dental implant abutment to the pre-existing dental implant in the patient during the first stage or the second stage of the dental implant surgery, the continuous outer surface of the frontward facing portion approximates the natural appearance of an anterior tooth of the patient and protrudes through the gum tissue of the patient and the ball component bypasses the anti-rotational feature of the re-existing dental implant.

2. The transitional anterior dental implant abutment of claim 1, wherein the occlusal ball component comprises a collar portion.

3. The transitional anterior dental implant abutment of claim 2, wherein the collar portion is configured to abut a shoulder area of the pre-existing dental implant.

4. The transitional anterior dental implant abutment of claim 2, wherein the collar portion has substantially the same diameter as the pre-existing dental implant.

5. The transitional anterior dental implant abutment of claim 1, wherein the occlusal ball component is configured to attach to the pre-existing dental implant by the screw.

6. The transitional anterior dental implant abutment of claim 1, wherein the crown component rotates in the labial direction and the lingual direction after snapping onto the ball component.

7. The transitional anterior dental implant abutment of claim 1, wherein the crown component comprises acrylic.

8. The transitional anterior dental abutment of claim 1, wherein the continuous outer surface of the frontward facing portion of the crown component has substantially an anatomical shape of a left upper cuspid, a right upper cuspid, left upper lateral incisor, right upper lateral incisor, left upper central incisor, right upper central incisor, left lower cuspid, right lower cuspid, left lower lateral incisor, right lower lateral incisor, left lower central incisor, or right lower central incisor.

9. The transitional anterior dental implant abutment of claim 1, wherein the occlusal ball component comprises a collar portion configured to directly abut a shoulder area of the pre-existing dental implant.

10. The transitional anterior dental implant abutment of claim 1, wherein the occlusal ball component comprises a collar portion configured to directly abut a shoulder area of the pre-existing dental implant, and wherein the occlusal ball component is configured to attach to the pre-existing dental implant by the screw.

11. A method for installing a transitional anterior dental implant abutment in a patient during a first stage or a second stage of a dental implant surgery, the transitional anterior dental implant abutment consisting of a ball component and a crown component, the method comprising:
    surgically placing a dental implant into a jaw of a patient;
    selecting the ball component of the transitional anterior dental implant abutment based on the size of the dental implant placed in the jaw;

attaching the ball component to the dental implant during the first stage or the second stage of the dental implant surgery, wherein the ball component bypasses an anti-rotational feature of the dental implant;

snapping the crown component onto the ball component during the first stage or the second stage of the dental implant surgery, wherein the crown component consists of a single, unitary structure having a frontward facing portion and a rearward facing portion, wherein the frontward facing portion defines a continuous outer surface which approximates the natural appearance of an anterior tooth and protrudes through gum tissue of the patient, wherein the rearward facing portion has an open slot, and wherein the crown component snaps onto the ball component such that the crown component directly contacts the ball component; and rotating the crown component into proper position.

12. The method of claim 11, further comprising, filling the crown component partially with resin material before snapping the crown component to the ball component;

setting the resin material after rotating the crown component into proper position; and removing excess resin material that may have exited the crown component through an open slot located in the crown component.

13. The method of claim 12, further comprising, polishing the crown component after removing the excess resin material.

14. The method of claim 11, further comprising splinting two or more crown components together.

15. A transitional anterior dental implant abutment for attachment to a pre-existing dental implant by a screw in a patient during a first stage or a second stage of a dental implant surgery, the transitional anterior dental implant abutment consisting of:

an occlusal ball component, wherein the ball component is configured to fit over and attach to the pre-existing dental implant and to bypass an anti-rotational feature of the pre-existing dental implant; and a crown component consisting of a single, unitary structure having a frontward facing portion and a rearward facing portion, wherein the frontward facing portion defines a continuous outer surface which approximates the natural appearance of an anterior tooth and is configured to protrude through gum tissue of the patient, wherein the rearward facing portion has an open slot, wherein the crown component snaps directly onto a ball portion of the ball component and directly contacts the ball portion, and wherein the crown component is rotatable in a labial and in a lingual direction on the ball component, such that:

upon attachment of the transitional anterior dental implant abutment to the pre-existing dental implant in the patient during the first stage or the second stage of the dental implant surgery, the continuous outer surface of the frontward facing portion of the crown component approximates the natural appearance of an anterior tooth of the patient and protrudes through the gum tissue of the patient and the ball component bypasses the anti-rotational feature of the pre-existing dental implant.

16. The transitional anterior dental implant abutment of claim 15, wherein the crown component is rotatable up to approximately 24° in a buccal labial direction on the ball component.

17. The transitional anterior dental implant abutment of claim 15, wherein the ball component comprises an opening, wherein the opening extends through a length of the ball component, wherein the opening is located substantially through the center of the ball component, and wherein the opening comprises a top section, a middle section, and a bottom section, wherein the middle section is narrower than the top section and the middle section is narrower than the bottom section.

* * * * *

UNITED STATES PATENT AND TRADEMARK OFFICE
CERTIFICATE OF CORRECTION

| | | |
|---|---|---|
| PATENT NO. | : 9,044,289 B2 | Page 1 of 1 |
| APPLICATION NO. | : 12/364031 | |
| DATED | : June 2, 2015 | |
| INVENTOR(S) | : Joseph Wiener | |

It is certified that error appears in the above-identified patent and that said Letters Patent is hereby corrected as shown below:

In The Claims

Col. 8, Claim 1, Line 21,
"feature of the re-existing dental implant." should read
--feature of the pre-existing dental implant.--

Signed and Sealed this
Twenty-ninth Day of March, 2016

Michelle K. Lee
*Director of the United States Patent and Trademark Office*